United States Patent
Reddy et al.

(10) Patent No.: US 8,406,899 B2
(45) Date of Patent: Mar. 26, 2013

(54) BUNDLE OF HIS STIMULATION SYSTEM

(75) Inventors: G. Shantanu Reddy, Minneapolis, MN (US); Matthew S. Finlay, Minneapolis, MN (US)

(73) Assignee: Cardiac Pacemakers, Inc., St. Paul, MN (US)

(*) Notice: Subject to any disclaimer, the term of this patent is extended or adjusted under 35 U.S.C. 154(b) by 0 days.

(21) Appl. No.: 13/422,622

(22) Filed: Mar. 16, 2012

(65) Prior Publication Data

US 2012/0179221 A1  Jul. 12, 2012

Related U.S. Application Data

(62) Division of application No. 12/424,298, filed on Apr. 15, 2009, now abandoned.

(60) Provisional application No. 61/045,168, filed on Apr. 15, 2008.

(51) Int. Cl.
*A61N 1/00* (2006.01)

(52) U.S. Cl. ......... 607/122; 607/119; 607/126; 607/127

(58) Field of Classification Search ................ 607/1–38, 607/115, 119–132
See application file for complete search history.

(56) References Cited

U.S. PATENT DOCUMENTS

| | | | |
|---|---|---|---|
| 4,258,724 A | 3/1981 | Balat et al. | |
| 5,429,131 A | 7/1995 | Scheinman et al. | |
| 5,450,846 A | 9/1995 | Goldreyer | |
| 5,534,022 A | 7/1996 | Hoffmann et al. | |
| 5,545,201 A * | 8/1996 | Helland et al. | 607/127 |
| 5,575,814 A | 11/1996 | Giele et al. | |
| 5,683,447 A | 11/1997 | Bush et al. | |
| 6,078,840 A | 6/2000 | Stokes | |
| 6,463,334 B1 | 10/2002 | Flynn et al. | |
| 6,609,027 B2 | 8/2003 | Kroll et al. | |
| 6,819,959 B1 | 11/2004 | Dean et al. | |
| 6,887,229 B1 * | 5/2005 | Kurth | 604/525 |
| 6,937,897 B2 | 8/2005 | Min et al. | |
| 6,990,378 B1 | 1/2006 | Algee | |
| 7,027,876 B2 | 4/2006 | Casavant et al. | |

(Continued)

FOREIGN PATENT DOCUMENTS

| | | |
|---|---|---|
| EP | 0 356 009 | 2/1990 |
| JP | 06070990 A | 3/1994 |

(Continued)

OTHER PUBLICATIONS

International Search Report and Written Opinion issued in PCT/US2009/040675, mailed Dec. 2, 2009, 20 Pages.

(Continued)

*Primary Examiner* — Niketa Patel
*Assistant Examiner* — Lindsey G Hankins
(74) *Attorney, Agent, or Firm* — Faegre Baker Daniels LLP

(57) ABSTRACT

A system for therapeutically stimulating a His bundle includes an implantable pulse generator and a multi-polar medical electrical lead. The generator is configured for subcutaneous implantation and to generate a pacing stimulus. The lead includes a connector assembly, a flexible tubular body, a distal tip assembly and coil conductors. The body extends intravascularly from the generator to a location proximate the His bundle and includes a proximal end, a distal end, and a longitudinal lumen. The tip assembly includes an electrode, a fixation helix, and a shank portion. The helix extends to a location proximate the His bundle and is operable as an electrically isolated electrode. The shank portion extends within the lumen and includes a receptacle for receiving a stylet tip. The conductors extend longitudinally through the lumen and are coupled to the electrode and the helix. One or both of the conductors defines a stylet lumen.

16 Claims, 6 Drawing Sheets

U.S. PATENT DOCUMENTS

| | | |
|---|---|---|
| 7,082,335 B2 | 7/2006 | Klein et al. |
| 7,092,766 B1 | 8/2006 | Salys et al. |
| 7,120,504 B2 | 10/2006 | Osypka |
| 7,130,682 B2 * | 10/2006 | Stahmann et al. ............... 607/9 |
| 7,155,292 B2 | 12/2006 | Kawula et al. |
| 7,158,838 B2 | 1/2007 | Seifert et al. |
| 7,162,310 B2 | 1/2007 | Doan |
| 7,177,704 B2 | 2/2007 | Laske et al. |
| 7,245,973 B2 | 7/2007 | Liu et al. |
| 7,257,449 B2 | 8/2007 | Bodner |
| 7,337,009 B2 | 2/2008 | Schell |
| 7,392,095 B2 | 6/2008 | Flynn et al. |
| 2002/0183820 A1 | 12/2002 | Schell |
| 2003/0083727 A1 | 5/2003 | Casavant et al. |
| 2004/0014355 A1 * | 1/2004 | Osypka et al. ............... 439/502 |
| 2004/0127967 A1 | 7/2004 | Osypka |
| 2004/0133259 A1 * | 7/2004 | Janke et al. ................. 607/127 |
| 2004/0147994 A1 | 7/2004 | Zhang et al. |
| 2005/0070984 A1 | 3/2005 | Sundberg |
| 2005/0085885 A1 | 4/2005 | Janke et al. |
| 2005/0137671 A1 | 6/2005 | Liu et al. |
| 2006/0142814 A1 | 6/2006 | Laske et al. |
| 2006/0293737 A1 | 12/2006 | Krishnan |
| 2007/0203555 A1 | 8/2007 | Williams |
| 2007/0208324 A1 | 9/2007 | Johnson |
| 2007/0233216 A1 | 10/2007 | Liu et al. |
| 2009/0259272 A1 | 10/2009 | Reddy et al. |

FOREIGN PATENT DOCUMENTS

| | | |
|---|---|---|
| JP | 9103495 A | 4/1997 |
| JP | 2000509300 A | 7/2000 |
| JP | 2001511407 A | 8/2001 |
| WO | WO 03/030988 | 4/2003 |
| WO | WO 03/092799 | 11/2003 |
| WO | WO2006045075 A1 | 4/2006 |

OTHER PUBLICATIONS

Physician's Manual, Endotak Reliance® G, Endotak Reliance® SG, © 2004 Guidant Corporation.

Physician's Manual, Flextend® Steroid-Eluting, Extendable/Retractable helix, Pace/Sense Leads, Models: 4086/4087/4088, © 2003 Guidant Corporation.

Williams et al., "Selective vs. non-selective His bundle pacing," Cardiovascular Research, 1976, 10: pp. 91-100.

European Search Report issued in EP Application No. 12176496, dated Oct. 31, 2012, 6 pages.

* cited by examiner

BUNDLE OF HIS STIMULATION SYSTEM

CROSS-REFERENCE TO RELATED APPLICATION

This application is a divisional of U.S. patent application Ser. No. 12/424,298, filed Apr. 15, 2009, entitled "Bundle of His Stimulation System," which claims priority under 35 U.S.C. §119 to U.S. Provisional Application No. 61/045,168, filed on Apr. 15, 2008, entitled "Bundle of HIS Stimulation System," each of which is incorporated herein by reference in its entirety.

TECHNICAL FIELD

The present invention relates to medical electrical leads for use in cardiac rhythm management systems. In particular, the present invention relates to medical electrical leads configured for mapping and pacing the bundle of His in a heart of a patient.

BACKGROUND

Cardiac rhythm management systems are useful for electrically stimulating a patient's heart to treat various cardiac arrhythmias. A proposed method of electrically stimulating the heart includes stimulating the His bundle located proximate to the apex of the triangle of Koch in the right atrium of the heart. By directly stimulating the bundle of His, both the right and left ventricles can be physiologically activated, potentially avoiding pacing induced dyssynchrony present with right ventricular apex pacing. There is a continuing need for improved His bundle lead designs and assemblies.

SUMMARY

In a first aspect, the present invention is a system for therapeutically stimulating a His bundle of a patient's heart including an implantable pulse generator and a multi-polar medical electrical lead. The implantable pulse generator is configured for subcutaneous implantation in the patient and to generate an electrical pacing stimulus. The lead is operatively coupled to the pulse generator to deliver the pacing stimulus to cardiac tissue proximate the His bundle and includes a proximal connector assembly, a flexible tubular body, a distal tip assembly and first and second coil conductors. The proximal connector assembly is configured to mechanically and electrically couple the lead to the pulse generator. The body is dimensioned to extend at least partially intravascularly from the pulse generator to a location proximate the His bundle. The body includes a proximal end coupled to the proximal connector, a distal end opposite the proximal end and a longitudinal conductor lumen extending from the proximal end of the body to the distal end of the body. The distal tip assembly is fixedly coupled to the distal end of the body and includes a first electrode spaced from the distal end of the body, a fixation helix, and a shank portion. The fixation helix is fixedly coupled to the lead body and extends distally of the first electrode. The fixation helix has a sharpened distal tip and is operable as a second electrode electrically isolated from the first electrode and is dimensioned to extend to a location proximate the His bundle. The shank portion extends proximally of the first electrode and the fixation helix within the conductor lumen and includes a proximal face having a receptacle for receiving and engaging a stylet tip. The first and second coil conductors extend longitudinally through the conductor lumen and are electrically and mechanically coupled to the first electrode and the fixation helix, respectively. Either one or both of the first and second coil conductors defines a stylet lumen.

In a second aspect, the present invention is a system including a pulse generator configured to generate an electrical pacing stimulus, a separable, splittable or slittable guide catheter configured to deliver electrical stimulation to a His bundle of a patient's heart, and an implantable medical electrical lead sized to be slidably received within an open lumen of the catheter. The catheter includes a proximal shaft having a proximal end, a pre-curved distal portion extending distally from the proximal shaft and terminating in a distal tip, an open lumen extending longitudinally from the proximal end of the shaft portion to the distal tip, at least one electrode proximate the distal tip, and an electrically conductive member extending from at least the proximal end of the shaft portion to the electrode. The pre-curved distal portion includes a series of contiguous pre-formed curved segments, each having a different radius of curvature and extending along a different arc length than each immediately adjacent segment. The distal portion is configured to locate the distal tip proximate an atrial wall of the heart adjacent the His bundle when the proximal shaft portion is at least partially located in a superior vena cava of the heart. The electrically conductive member electrically couples the electrode to an external device for mapping electrical activity of the heart. The implantable medical electrical lead includes a proximal connector assembly configured to mechanically and electrically couple the lead to the pulse generator, a flexible tubular body, a distal tip assembly, first and second coil conductors and a stylet. The flexible tubular body is dimensioned to extend at least partially intravascularly from the pulse generator through the patient's superior vena cava to a location proximate the His bundle. The body includes a proximal end coupled to the proximal connector, a distal end opposite the proximal end, and a longitudinal conductor lumen extending from the proximal end of the body to the distal end of the body. The distal tip assembly is fixedly coupled to the distal end of the body and includes a first electrode positioned adjacent to the distal end of the body, a fixation helix fixedly coupled to the body and extending distally of the first electrode, and a shank portion extending proximally of the first electrode and the fixation helix within the conductor lumen. The fixation helix is operable as a second electrode electrically isolated from the first electrode and is further dimensioned to extend from a wall of a right atrial septum to a location proximate the His bundle. The shank portion includes a proximal face having a receptacle for receiving and engaging a stylet tip. The first and second coil conductors extend longitudinally through the conductor lumen and are electrically and mechanically coupled to the first electrode and the fixation helix, respectively. Either one or both of the first and second coil conductors defines a stylet lumen. The stylet has a proximal end and a distal end including an engaging feature configured to mate with and engage the receptacle on the shank portion of the lead distal tip assembly. The stylet is configured to transmit a torque applied at its proximal end to the distal tip assembly to cause rotation of the fixation helix and the lead body.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
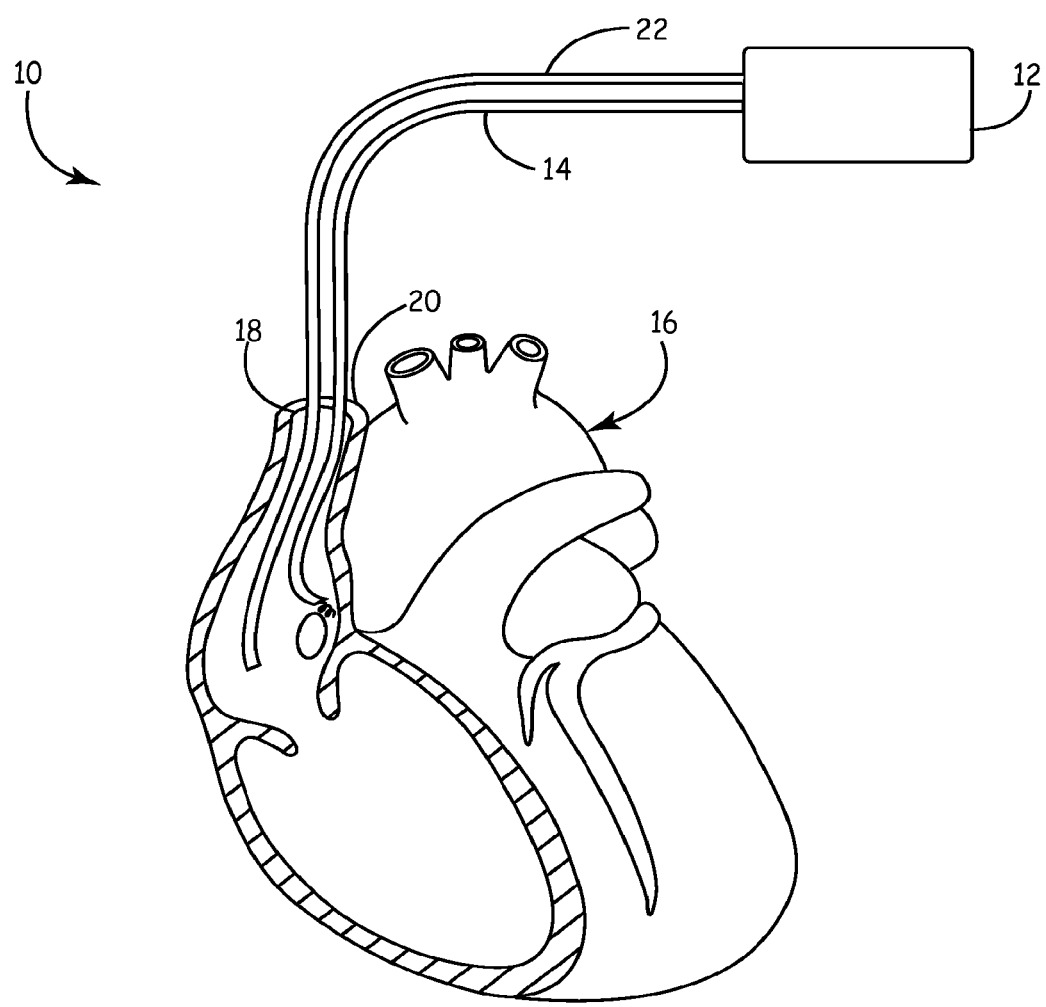
FIG. 1 is a schematic view of a His bundle stimulation and pacing system including a pulse generator and a lead implanted in a patient's heart according to an embodiment of the present invention.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a schematic view of a His bundle mapping and pacing system 10 ("His bundle system 10") according to an embodiment of the present invention. As shown in FIG. 1, the His bundle system 10 includes an implantable pulse generator 12 coupled to a His bundle lead 14 deployed in a patient's heart 16. The pulse generator 12 generates an electrical pacing stimulus to be delivered to the heart 16. The lead 14 operates to convey electrical signals and stimuli between the heart 16 and the pulse generator 12. As further shown in FIG. 1, the heart 16 includes a right atrium and a right ventricle separated by a tricuspid valve. During normal operation of the heart 16, deoxygenated blood is fed into the right atrium through the superior vena cava 18 and the inferior vena cava. The major veins supplying blood to the superior vena cava 18 include the right and left axillary veins, which flow into the right and left subclavian veins. The right and left external jugular veins of the heart, along with the right and left internal jugular veins of the heart, join the right and left subclavian veins to form the right and left brachiocephalic veins, which in turn combine to flow into the superior vena cava.

As shown, the lead 14 enters the vascular system through a vascular entry site 20 formed in the wall of the left subclavian vein, extends through the left brachiocephalic vein and the superior vena cava 18, and is implanted in the right atrium. In other embodiments of the present invention, the lead 14 may enter the vascular system through the right subclavian vein, the left axillary vein, the left external jugular, the left internal jugular, or the left brachiocephalic vein. In still other embodiments, other suitable vascular access sites may be utilized. In short, any suitable venous path may be utilized for delivering the lead 14 to the desired implantation site.

In the illustrated embodiment, the lead 14 is implanted in the right atrium proximate to the apex of the triangle of Koch. The His bundle system 10 allows direct therapeutic stimulation of the His bundle by fixating a lead proximate to the apex of the triangle of Koch. Once the His bundle has been located through one of various mapping techniques, the His bundle is directly stimulated through the right atrium of the heart. Although the His bundle system 10 is described as stimulating and pacing the His bundle, the His bundle system 10 may also be used in other applications, such as right ventricular septal placement, without departing from the intended scope of the present invention.

The lead 14 facilitates obtaining selective His bundle pacing (SHBP) where His capture thresholds are low and ventricular capture thresholds are high. In the case of SHBP, the His potential recorded by the lead 14 should be near field and high amplitude. Alternatively, the lead 14 can also be used for Parahisian pacing (PHP), where His capture thresholds are high and ventricular capture thresholds are low. With PHP, the His potential recorded by the lead 14 should be far field and low in amplitude.

In the illustrated embodiment, a second right atrial lead 22 is situated in the right atrium, as is known for conventional cardiac rhythm management systems. In another embodiment, the His bundle system 10 is a three lead system having a right ventricular lead (not shown) in addition to the His bundle lead 14 and the right atrial lead 22. While the His bundle lead 14 stimulates the His bundle, if His capture is not maintained or is unreliable, suitable ventricular capture could also be maintained by the right ventricular lead. If the His bundle lead 14 is faulty, the right ventricular lead acts as a back up to the His bundle lead 14. For example, the His bundle system 10 could be configured such that the back up right ventricular lead would pace if it sensed a lack of contraction, otherwise it would lay dormant. The His bundle system 10 may also include additional leads depending on the particular therapeutic needs of the patient. For example, in various embodiments, the His bundle system 10 includes a lead extending into a coronary vein for stimulating the left ventricle in a bi-ventricular pacing or cardiac resynchronization therapy system. Alternatively or additionally, one or more cardioversion/defibrillation leads (not shown) can also be included in the His bundle system 10, in which case the pulse generator 12 will include defibrillation capabilities.

Figure 2A:
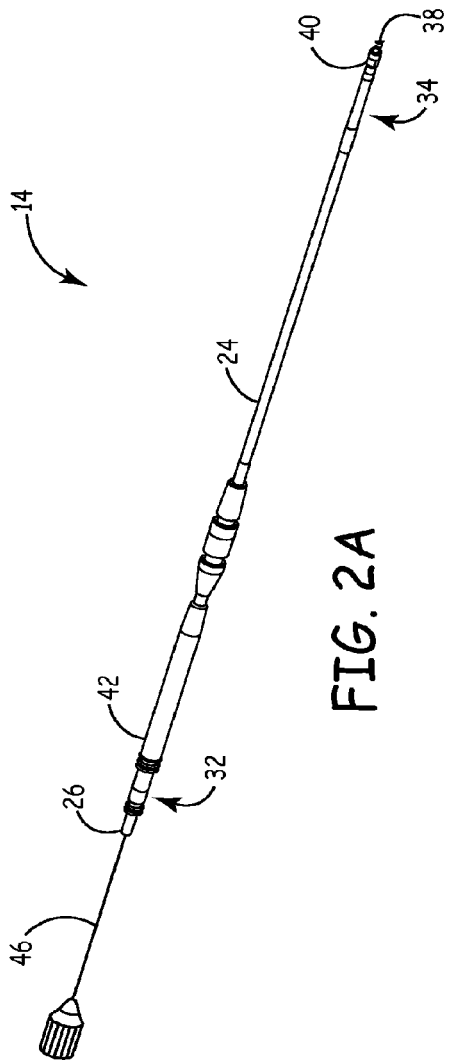
FIG. 2A is a plan view of a lead of the His bundle stimulation and pacing system of FIG. 1 according to an embodiment of the present invention.
Figure 2B:
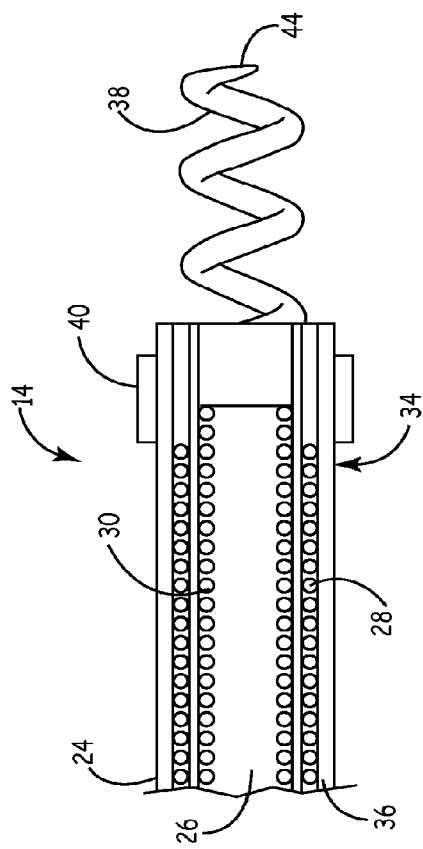
FIG. 2B is a cross-sectional view of the lead of FIG. 2A according to an embodiment of the present invention.

FIGS. 2A and 2B are isometric and partial cross-sectional views, respectively, of the lead 14 of the His bundle system 10 according to one embodiment of the present invention. As shown, the lead 14 is a multi-polar medical electrical lead and includes a lead body 24, a stylet lumen 26, a first coil conductor 28 and a second coil conductor 30. The lead body 24 is a flexible tubular body including a proximal end 32 and a distal end 34, and defines a conductor lumen 36 extending between the proximal and distal ends 32, 34. The coil conductors 28, 30 extend longitudinally within the conductor lumen 36. In the illustrated embodiment, the coil conductors 28, 30 are arranged coaxially, with the conductors 28, 30 defining the stylet lumen 26.

As shown, the lead 14 further includes a fixation helix 38 extending distally from the distal end 34 of the lead body 24, and a proximal electrode 40 located at the distal end 34 of the lead body 24 and spaced from the fixation helix 38. Additionally, the proximal end 32 of the lead body 24 is connected to a proximal connector assembly 42 configured to mechanically and electrically couple the lead 14 to the pulse generator 12 (shown in FIG. 1). As shown, the coil conductors 28, 30 are coupled to the proximal electrode 40 and the fixation helix 38, respectively. As will be appreciated, the coil electrodes 38, 40 are also electrically coupled to individual electrical contacts in the connector assembly 42.

The fixation helix 38 is a fixed helix having a sharpened tip portion 44 and is electrically active to function as the cathode electrode. In one embodiment, the tip portion 44 of the fixation helix 38 is flat ground to enable better penetration through the fibrous His bundle and is sufficiently long to penetrate through the central fibrous body of the heart 16 and contact the His bundle. In an exemplary embodiment, the fixation helix 38 is about 2.5 mm long (measured from the lead body 24 to the tip of the fixation helix 38 along the general axis of the lead 14). In various embodiments, the lead body 24 is configured to have sufficient torsional stiffness to allow as much direct torque transfer as possible to allow penetration of the relatively tough central fibrous body proximate the His bundle with the fixation helix 38. The application of torque typically occurs by the user at the proximal connector assembly 42 or at the lead body 24 proximate the proximal connector assembly 42. In an exemplary embodiment, the lead 14 has as close to infinite torsional stiffness as possible and a torque transfer of about 1:1 such that one turn of the proximal connector assembly 42 or lead body 24 is transferred to the fixation helix 38 with no to minimal attenuation, even when penetrating the fixation helix 38 into a tough structure, such as fibrous tissue. An approximate 1:1 torque transfer ratio enables precise control over the fixation process into the fibrous tissue, enabling the physician to stop when the His potential is maximized.

The fixation helix 38 is optionally coated with a polymer-drug, such as an anti-inflammatory agent, that is durable and able to withstand fixation of the fixation helix 38. In one embodiment, the fixation helix 38 includes a durable steroid-polymer matrix capable of withstanding positioning and repositioning in the fibrous bundle. In addition, the steroid-polymer matrix also reduces inflammation associated with the fixation process and promotes high pacing thresholds. Examples of suitable steroid-polymer matrices include, but are not limited to: paclitaxel, clobetasol and dexamethasone.

The stylet lumen 26 enables the use of a stiffening stylet wire 46 to deliver the lead 14 to the desired location. If the lead 14 dislodges from the heart 16, the stylet lumen 26 also allows the lead 14 to be repositioned without having to remove the lead 14, reaccess the vein, and place a new catheter. In one embodiment, the stylet lumen 26 may be configured to receive a locking stylet which allows the lead 14 to be more easily extracted if needed. In an alternative embodiment, the stylet lumen 26 may be sized to accommodate a torque tube design, rather than a traditional stylet wire. While the lead 14 is discussed as including a stylet lumen 26, in an alternative embodiment, the lead 14 may be a lumenless lead without departing from the intended scope of the present invention.

In one embodiment, the lead 14 is fixated in the heart 16 by rotating the lead body 24 to screw the helix 38 into the heart tissue. When implanted, the tip portion 44 of the fixation helix 38 extends from a wall of the right atrial septum to the His bundle. Because the lead 14 includes a fixed helix 38, the lead body 24 is configured to provide efficient torque transfer from the proximal end 32 of the lead body 24 to the fixation helix 38, so as to penetrate through the central fibrous body at the triangle of Koch. In order to fixate the fixed helix 38 at the bundle of His, the lead body 24 is turned such that torque is transferred down the lead body 24, resulting in rotation of the fixed fixation helix 38 of the lead 14. In one embodiment, the lead body 24 is sufficiently lubricious to facilitate the passage of the lead 14 and torque transfer to the lead body 24. In an exemplary embodiment, the lead body 24 is formed of polyurethane to enable torque transfer and also to provide the desired lubricity. In another embodiment, the lead body 24 is formed of silicone which may or may not include a lubricious coating or treatment to increase lubricity and also may be reinforced to enhance torque transfer. Although the fixation helix 38 is discussed as being a fixed helix, in an alternative embodiment, the fixation helix 38 is an extendable-retractable helix.

Alternatively, the lead body 24 and fixation helix 38 can be rotated with a bladed stylet configured to engage a feature at the distal end 34 of the lead 14 (shown in FIG. 3 below). In another embodiment, a stylet can be keyed to a terminal pin to separately facilitate torque transfer. In one embodiment, a torque tube having a keyed end could be used to mate with a receptacle in the lead tip.

In the illustrated embodiment, the lead 14 of the His bundle system 10 includes dual coil conductors arranged coaxially within the lead body 24. In other embodiments, other conductor configurations may be employed. For example, a bipolar lead may include a co-radial design, or alternatively, may have dual cables, one on either side of a center lumen. The center lumen is only used for stylet passage and either a dummy coil or a polymer sheath is used for stylet puncture protection. In another embodiment, the lead is a multi-polar lead including longitudinally spaced third and fourth electrodes coupled proximal to the distal end of the lead. The third and fourth electrodes are mechanically and electrically coupled to third and fourth conductors. In this embodiment, the third and fourth conductors may be positioned within a second conductor lumen of the lead. The lead may also include a third conductor lumen such that the third conductor is positioned within the second conductor lumen and the fourth conductor is positioned within the third conductor lumen. The multi-polar lead may also include a co-radial coil flanked by two cables or two cables running in one lumen; a quad-filar co-radial design; a trifilar co-radial inner coil; an outer flat wire coil that provides torque transfer and enables a size reduction over a round wire; and a design with four cables flanking a center lumen. Examples of co-radial designs are further described in co-pending U.S. Patent Publication No. 20060293737 entitled "Multiple Electrode Implantable Lead", which is hereby incorporated by reference. Still other lead body and conductor configurations will become apparent to those of skill in the art.

Figure 3:
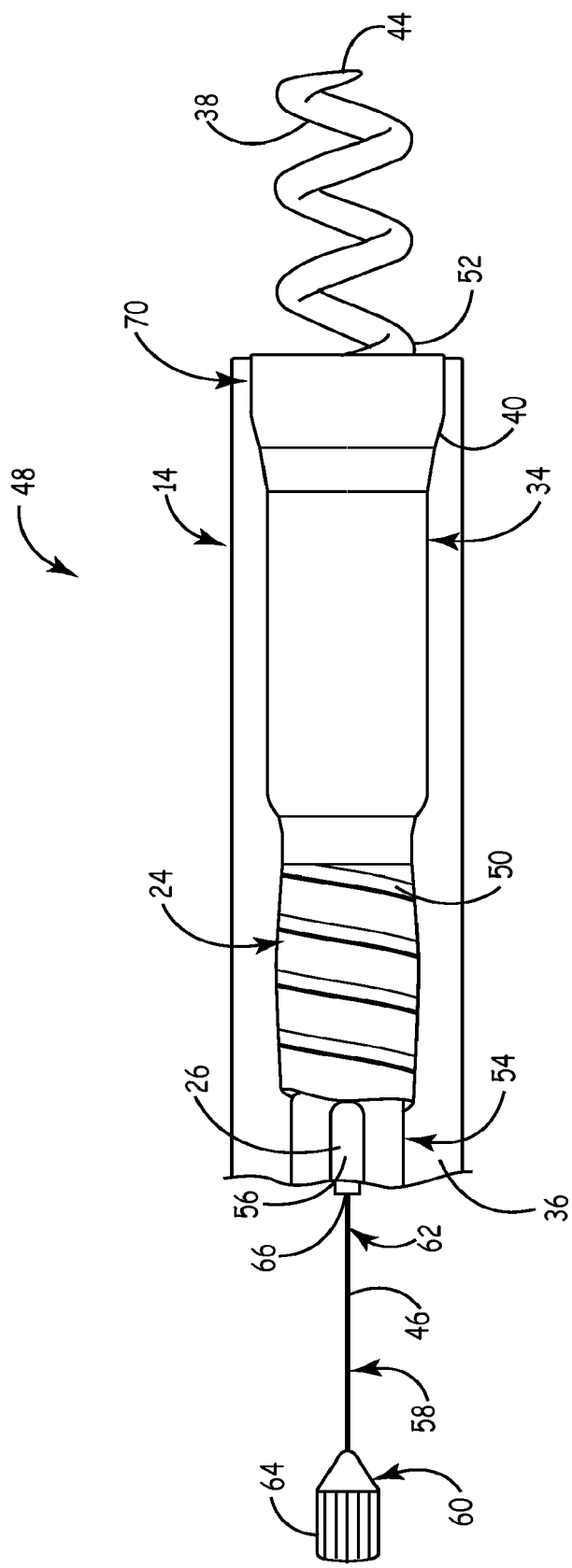
FIG. 3 is a side view of a distal tip assembly of the lead of FIGS. 2A and 2B according to an embodiment of the present invention.

FIG. 3 is a side view of a distal tip assembly 48 configured to be incorporated into the His bundle lead 14. As shown in FIG. 3, the distal tip assembly 48 includes the fixation helix 38, the proximal electrode 40 and a shank portion 50 and is configured to be coupled to the distal end 34 of the lead body 24, with the shank portion 50 received by the conductor lumen 36 of the lead body 24. The proximal electrode 40 is spaced from the distal end 34 of the lead body 24 and the fixation helix 38 extends distally of the proximal electrode 40. As discussed above, the fixation helix 38 can function as a second electrode that is electrically isolated from the proximal electrode 40. To isolate the first and second electrodes 38, 40, an insulating material 52 may be disposed between the electrodes 38, 40. In an exemplary embodiment, the insulating material 52 is a masking layer applied proximate the proximal electrode 40. The proximal electrode 40 is electrically and mechanically connected to the first coil conductor 28 (shown in FIG. 2B) and the fixation helix 38 is electrically and mechanically connected to the second coil conductor 30 (shown in FIG. 2B).

The shank portion 50 of the distal tip assembly 48 extends within the conductor lumen 36 of the lead body 24 proximally of the proximal electrode 40 and the fixation helix 38. The shank portion 50 includes a proximal face 54 having a recess 56 for receiving and engaging the tip of a bladed stylet, such as the stiffening stylet wire 46. The stiffening stylet wire 46 includes a shaft 58 having a proximal end 60 and a distal end 62. The proximal end 60 includes a handle 64 and the distal end 62 includes an engagement member 66 that is configured to mate with and engage the recess 56 of the shank portion 50 of the distal tip assembly 48. The stiffening stylet wire 46 is configured to transmit a torque applied at the handle 64 to the distal tip assembly 48 to rotate the lead body 24 and the fixation helix 38. Precise application of torque through the lead body 24 into the heart 16 occurs by engaging the engagement member 66 of the stiffening stylet wire 46 with the recess 56 and rotating the stiffening stylet wire 46. In an exemplary embodiment, the recess 56 has a linear slot configuration.

As shown, the distal tip assembly 48 includes a blunt tip 70 to prevent over-extension or penetration into the heart tissue when the lead 14 is being implanted. The proximal electrode 40 is located on the blunt tip 70 and the fixation helix 38 extends distally of the blunt tip 70.

Although the entire fixation helix 38 has been discussed as being electrically active, in an alternative embodiment, only the tip portion 44 of the fixation helix 38 is active and the rest of the fixation helix 38 is coated with an insulator to prevent ventricular capture. With this configuration, the lead 14 can be fixated until a near field His bundle signal is obtained. In this embodiment, because only the tip portion 44 of the fixation helix 38 is electrically active, only low output His capture is obtained. As the fixation helix 38 is advanced into the cardiac tissue during fixation, the His potential may be mapped and the lead 14 can be continually repositioned until His capture is obtained. Once a near field His signal is recorded, further advancement of the fixation helix 38 into the tissue can be discontinued. Any suitable, biocompatible electrical insulative material (i.e. parylene) can be used as the insulating material.

In one embodiment, the shaft 58 of the stiffening stylet wire 46 is configured to radially expand when torque is applied to the stiffening stylet wire 46. Upon expansion, the shaft 58 is configured to frictionally engage an inner wall of the stylet lumen 26 and to transfer torque to the stylet lumen 26. In yet another embodiment, the stiffening stylet wire 46 includes a torque tube in which there are two overlapping helical coils—an inner coil and an outer coil. When rotated, the inner coil expands against the outer coil and creates a torque transfer system in a flexible shaft. When counter-rotated, the inner coil radially contracts and axially compresses to a solid stacked height to provide torque transfer in a flexible shaft. In yet another embodiment, the stylet lumen 26 may be a ribbon wire and/or the coil of the lead 14 may be a ribbon wire. The ribbon wire shape provides more efficient torque transfer than conventional circular systems.

Figure 4:
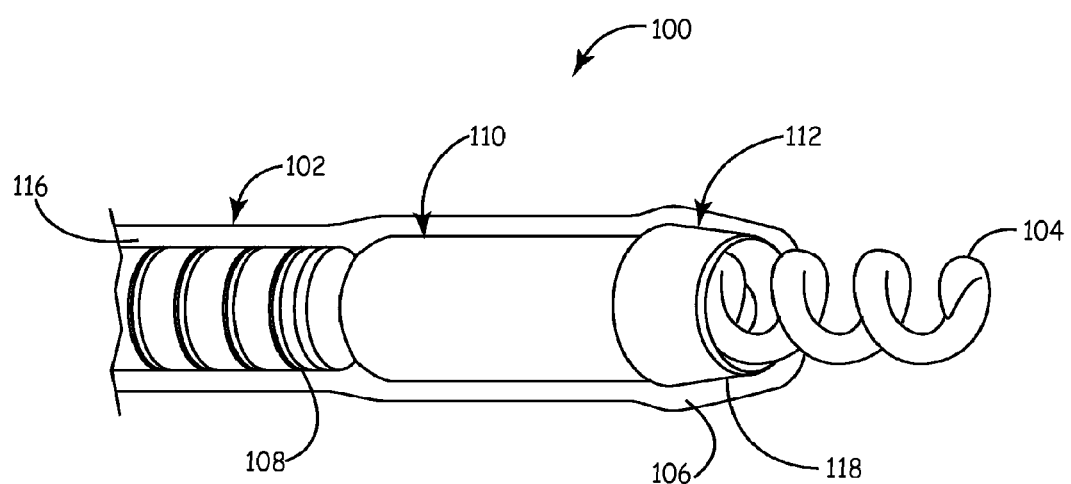
FIG. 4 is a perspective view of a bullet-nose distal tip assembly of the His bundle stimulation and pacing system of FIG. 1 according to an embodiment of the present invention.

FIG. 4 is a side view of a bullet-nose distal tip assembly 100 for inclusion in a lead 102 configured for use with the His bundle system 10 according to another embodiment of the present invention. The distal tip assembly 100 includes a helix 104, a proximal electrode 106 and a shank portion 108. The lead 102 includes a lead body 110 having a distal end 112 and a proximal end 114 (not shown) with a conductor lumen 116 extending between the distal end 112 and the proximal end 114. The shank portion 108 of the distal tip assembly 100 is configured to be coupled to the distal end 112 of a lead body 110 with the shank portion 108 received by the conductor lumen 116 of the lead body 110. The proximal electrode 106 is spaced from the distal end 112 of the lead body 110 and the helix 104 extends distally of the proximal electrode 106. The bullet-nose distal tip assembly 100 is substantially the same as the blunt tip distal tip assembly 48 (shown in FIG. 3) except that the distal end 112 of the lead 102 is bullet-nosed rather than blunt tipped. When the transition area between the lead body 110 and the helix 104 is bullet shaped, the helix 104 can function as the cathode and a tapered tip 118 of the distal end 112 formed by the bullet-nose can function as the anode. In one embodiment, the bullet-nosed tip is electrically active to form the proximal electrode 106. The coil conductors are coupled to the helix 104 and the proximal electrode 106, for example, by welding or crimping. With this configuration, if SHBP cannot be obtained, the tapered tip 118 can be switched to be the cathode, enabling ventricular pacing. The bullet-nose design illustrated in FIG. 4 enables deeper penetration of the distal end 112 into the heart tissue. This configuration may be particularly applicable with a double wire helix with programmable polarity to either enable a very discrete His potential or to enable electronic repositioning to find a better His potential without having to actually reposition the lead 102. For a double wire helix, the two wires are insulated through a fitting before connecting the wires to the coil conductor.

Figure 5:
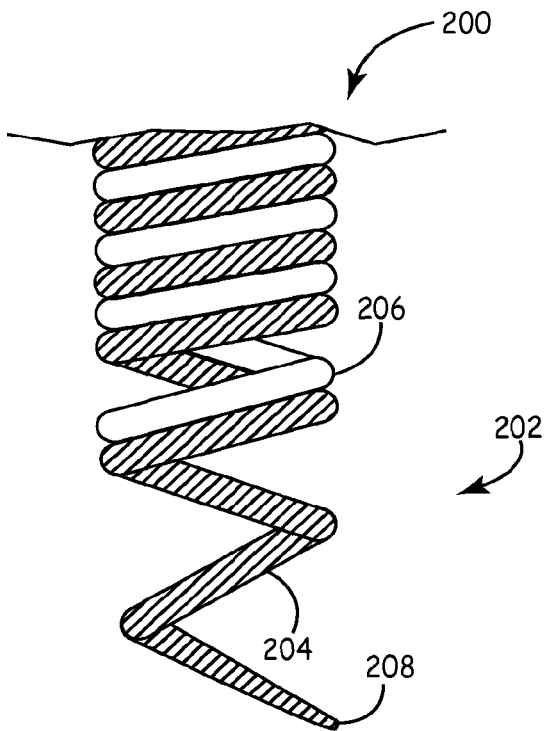
FIG. 5 is an enlarged view of a double helix of a distal tip assembly of the His bundle stimulation and pacing system of FIG. 1 according to an embodiment of the present invention.

FIG. 5 is an enlarged view of a double wire, bipolar fixation helix assembly 200 for use in a lead 202 configured to be incorporated into the His bundle system 10 according to another embodiment of the present invention. In this embodiment, the fixation helix assembly 200 includes a distal wire 204 and a proximal wire 206 close wound together. In an exemplary embodiment, the distal wire 204 and the proximal wire 206 are fixedly coupled together. The distal wire 204 operates as a distal electrode for His bundle pacing, while the proximal wire 206 operates as a proximal electrode for ventricular pacing. However, if the His bundle cannot be found and the lead 202 must be repositioned, the distal wire 204 and the proximal wire 206 can temporarily switch functions. The distal wire 204 includes a sharpened tip 208 for easy and atraumatic tissue penetration of the heart. The proximal wire 206 is spaced from the distal tip 208 of the distal wire 204 but still includes a sharpened distal tip 208 to allow for further penetration of the lead 202. In this configuration, the cathode and the anode are both in the distal wire 204. The distal wire 204 and the proximal wire 206 are conductors and are optionally selectively coated with an insulator to give separate conductor paths. Although FIG. 5 depicts the conductors 204 and 206 as being close wound for part of their length, both conductors 204 and 206 may optionally not be close-wound for part of their length.

Figure 6:
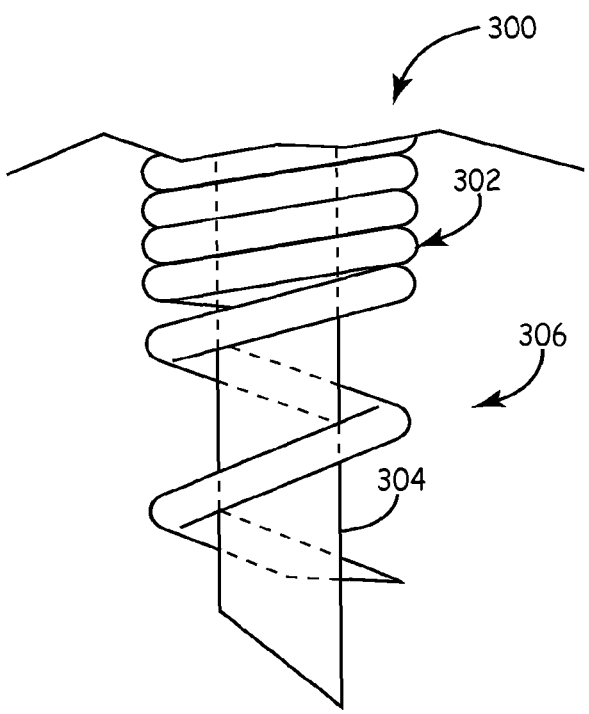
FIG. 6 is an enlarged view of a helix with an electrode of a distal tip assembly of the His bundle stimulation and pacing system of FIG. 1 according to an embodiment of the present invention.

FIG. 6 is a schematic view of an alternative helix/electrode assembly 300 for a His bundle pacing lead, such as the lead 14, having a helix 302 and an electrode 304, whereby the helix 302 is a fixed helix 302 and the electrode 304 is an extendable-retractable conductor needle. The helix 302 and the needle 304 of the assembly 300 have different conduction paths. The helix 302 functions similarly to the fixation helix 38 described in FIG. 2 and fixates the lead 306 to the heart 16 (shown in FIG. 1), providing anchoring stability to the lead 306. The needle 304 is operable to map the His bundle potential and is longitudinally extendable past the helix 302. Because the needle 304 is positioned within the helix 302, the needle 304 has an outer diameter sufficiently smaller than the inner diameter of the helix 302 to permit the needle 304 to translate longitudinally through the helix 302. The extendable-retractable needle 304 drives through the helix 302 upon rotating the terminal pin (shown in FIG. 2A) to provide accurate placement of the electrode/needle 304 near the His bundle (shown in FIG. 1). The needle 304 is pushed into the central fibrous body until it reaches the His bundle. The helix 302 is then screwed into the central fibrous body so as to anchor the lead 306 to the heart 16. Although FIG. 6 depicts the needle 304 as having a substantially tubular body and an angled tip, the needle 304 can have any variety of shapes for penetrating into the cardiac central fibrous body.

Figure 7:
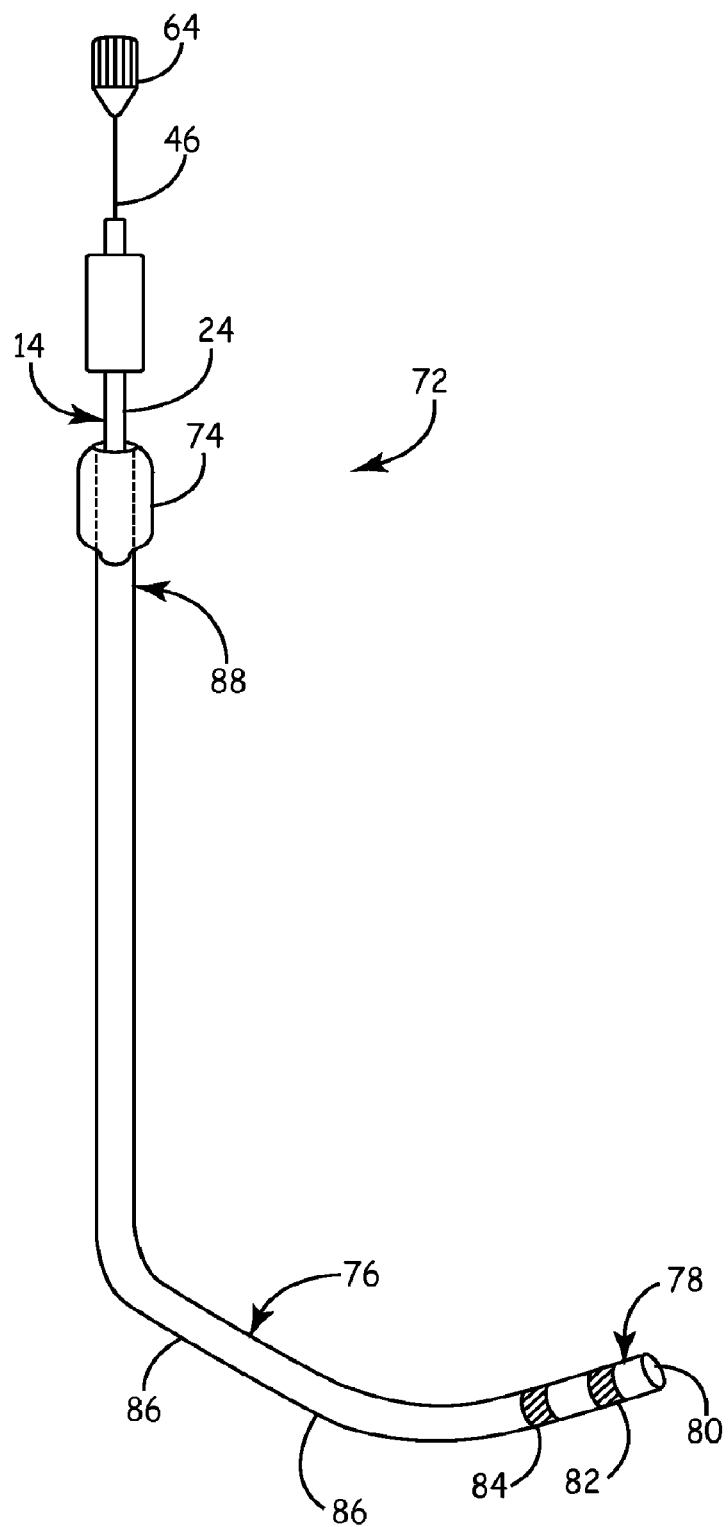
FIG. 7 is a schematic view of a delivery catheter of the His bundle stimulation and pacing system of FIG. 1 according to an embodiment of the present invention.

FIG. 7 is a schematic view of a lead delivery catheter 72 configured for locating the His bundle and delivering the His bundle pacing lead 14 to the desired implantation location. In the illustrated embodiment, the delivery catheter 72 is a fixed shape catheter having a preformed shape to enable orientation of the delivery catheter 72 proximate the coronary sinus at the apex of the triangle of Koch. The delivery catheter 72 includes a proximal shaft 74, a curved distal portion 76 having a distal end 78, an open lumen 80, an electrode 82 located at the distal end 78, and an electrically conductive member 84 extending within the catheter wall. The curved distal portion 76 includes a plurality of curved segments 86 and extends distally from the proximal shaft 74 and terminates at the distal tip 78. Each of the curved segments 86 has a radius of curvature and extends along an arc length. Generally, the radius of curvature and arc length of adjacent segments 86 are different from one another. The curved distal portion 76 is configured such that the distal end 78 can be positioned proximate an atrial wall of the heart 16 adjacent the bundle of His when the proximal shaft 74 is positioned within the superior vena cava 18 of the heart 16.

Because the apex of the triangle of Koch is proximate to the coronary sinus, the delivery catheter 72 is, in various embodiments, shaped in a manner similar to catheters configured for accessing the coronary sinus for left ventricular lead delivery. Embodiments of such catheters are described in co-pending and commonly assigned U.S. patent application Ser. No. 10/916,353 filed Aug. 11, 2004 and titled "Coronary Sinus Lead Delivery Catheter," which is incorporated herein by reference in its entirety. Of course, in other embodiments, other catheter shapes may be employed to locate the apex of the triangle of Koch and in turn, the His bundle.

In one embodiment, the electrode 82 of the delivery catheter 72 is located proximate the distal end 78 and facilitates direct His bundle mapping. The electrically conductive member 84 extends from at least a proximal end 88 of the proximal shaft 74 to the electrode 82 and electrically couples the electrode 82 to an external device for mapping electrical activity of the heart 16. Alternatively, the lead 14 could be used to map the His potential if connected to a 12-lead ECG.

The open lumen 80 of the delivery catheter 72 extends longitudinally from the proximal end 88 of the proximal shaft 74 to the distal end 78 of the curved distal portion 76. In practice, the lead 14 is passed through the lumen 80 of the delivery catheter 72 to the desired location. In one embodiment, the distal tip 78 of the delivery catheter 72 is generally more stiff than catheters used to deliver left ventricular leads so that once the distal end 78 of the delivery catheter 72 is oriented at the desired location, the lead 14 will not deflect the distal end 78 of the delivery catheter 72 away from the desired location as it is being passed through the delivery catheter 72. The inner diameter of the delivery catheter 72 in one embodiment includes a lubricious surface to facilitate passing the lead 14 through the delivery catheter 72 to allow rotation of the lead 14 to enable fixation of the lead 14.

The delivery catheter 72 has a separable, splittable or slittable configuration such that once the lead 14 has been properly placed and fixated, the delivery catheter 72 can be easily removed from the heart 16. For example, the delivery catheter 72 may have a peel-away configuration such that after the lead 14 has been placed within the cardiac tissue of the heart 16, the delivery catheter 72 can be easily split apart and removed from around the lead body 24 as it is being pulled from the heart 16. In the case that the delivery catheter 72 is braided, the delivery catheter 72 may have a cut-away configuration for use with a cutter. As the delivery catheter 72 is pulled back from the lead body 24, the cutter creates a slit through the delivery catheter 72 and allows the delivery catheter 72 to be separated from the lead body 24.

In another embodiment, a dual catheter system is used to place the lead 14 at the desired location. In a dual catheter system, an outer shaped catheter is introduced into the heart 16 and an inner catheter is passed through the outer catheter. This configuration allows a measure of deflectability and the inner catheter may have another shape enabling additional positioning of the lead 14 at the apex of the triangle of Koch. The lead 14 is then passed through the inner catheter to map the His bundle potential and to fixate in the heart.

In yet another embodiment, a deflectable catheter is used to place the lead 14 at the His bundle. A deflectable catheter allows the distal end 78 of the catheter to be manipulated when positioned within the heart 16. To manipulate the distal end 78, the proximal end 88 of the proximal shaft 74 includes a steering or deflection mechanism, such as pull wires. The steering mechanism allows the distal end 78 of the catheter to be maneuvered until properly positioned at the bundle of His.

In an embodiment where the delivery catheter 72 does not include electrodes, to properly orient the delivery catheter 72 within the heart 16, the His bundle may first be mapped via an EP deflectable catheter to locate a high amplitude His potential. Once the EP catheter has mapped the His bundle, the delivery catheter 72 is passed into the heart 16 and manipulated such that the distal end 78 of the delivery catheter 72 touches, or is proximate to, the tip of the EP deflectable catheter. The lead 14 is then passed through the delivery catheter 72 with a support wire or a torque transfer wire. When the distal end 34 (shown in FIG. 2) of the lead 14 is in place, the lead 14 is fixated by applying torque to the lead body 24 and the stiffening stylet wire 46 while continuing to map the His bundle. The handle 64 of the stiffening stylet wire 46 is rotated to control the deflection of the lead body 24. Fixation is accomplished by turning the entire lead body 24 while continuing to map in real-time. Application of torque continues until the highest amplitude His potential is found. If the resulting location of the distal end 34 of the lead 14 is accurately placed, the stiffening stylet wire 46 is removed. The delivery catheter 72 is then either cut or peeled away, depending on the configuration of the delivery catheter 72. After the lead 14 is fixated, the location of the lead 14 is optionally reassessed to ensure proper fixation of the lead 14.

The His bundle mapping and stimulation system of the present invention provides a time efficient system for locating and directly stimulating the His bundle. The His bundle system includes a lead that is introduced into the right atrium of the heart through a delivery catheter. Before the lead is passed through the delivery catheter, the location of the His bundle is mapped either by an EP catheter or some other means. In order to facilitate fixation into the bundle of His, which is formed of a central fibrous body, a distal end of the lead is a fixed helix and a proximal end of the lead includes a slot. To provide enough torque to rotate the entire lead body, a tool having an end sized to engage the slot is affixed to the proximal end of the lead and together the tool and the lead body are rotated. As a result of the rotation of the lead body, the fixed helix at the distal end of the lead is implanted into the bundle of His.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

The invention claimed is:

1. A system for therapeutically stimulating a His bundle of a patient's heart, the system comprising:
    an implantable pulse generator configured for subcutaneous implantation in the patient and to generate an electrical pacing stimulus; and
    a multi-polar medical electrical lead operatively coupled to the pulse generator for delivering the pacing stimulus to cardiac tissue proximate the His bundle, the lead comprising:
        a proximal connector assembly configured to mechanically and electrically couple the lead to the pulse generator;
        a flexible tubular body dimensioned to extend at least partially intravascularly from the implantation site of the pulse generator through a superior vena cava of the patient to a location proximate the His bundle, the body including a proximal end coupled to the proximal connector, a distal end opposite the proximal end and a longitudinal conductor lumen extending from the proximal end of the body to the distal end of the body;
        a distal tip assembly fixedly coupled to the distal end of the body, the tip assembly comprising:
            a first electrode spaced from the distal end of the body;
            a fixation helix fixedly coupled to the body and extending distally of the first electrode, the fixation helix configured as a second electrode electrically isolated from the first electrode, the fixation helix further dimensioned to extend from a wall of a right atrial septum of the patient to a location proximate the His bundle and including a sharpened distal tip; and
            a shank portion extending proximally of the first electrode and the fixation helix within the conductor lumen of the body, the shank portion including a proximal face having a receptacle for receiving and engaging a stylet tip,
            wherein the distal tip assembly includes a tapered distal tip, wherein the fixation helix extends distally of the tapered distal tip, and wherein the first electrode is located on the tapered distal tip;
        a first coil conductor extending longitudinally through the conductor lumen of the body and electrically and mechanically coupled to the first electrode; and
        a second coil conductor extending longitudinally through the conductor lumen of the body and electrically and mechanically coupled to the fixation helix,
        wherein one or both of the first and second coil conductors defines a stylet lumen.

2. The system of claim 1, wherein an insulating material is disposed between the first electrode and the fixation helix to electrically isolate the first electrode and the fixation helix.

3. The system of claim 2, wherein the insulating material is a masking layer on a portion of the fixation helix proximate the first electrode.

4. The system of claim 1, wherein the fixation helix includes an electrically insulating masking material along a portion of the fixation helix adjacent to the second electrode, wherein the masking material terminates proximal to the distal tip of the fixation helix.

5. The system of claim 1, wherein the first and second coil conductors are co-axially disposed, and wherein the first conductor is disposed about the second conductor.

6. The system of claim 1, wherein the first and second electrodes are co-radially disposed.

7. The system of claim 1, wherein the receptacle in the face of the shank portion is in the shape of a linear slot configured to receive and engage a bladed stylet tip.

8. The system of claim 1, wherein a torque transfer ratio of the body and the fixation helix is about 1:1.

9. The system of claim 1, wherein the lead further comprises:
    longitudinally spaced third and fourth electrodes coupled to the lead body proximal to the distal tip assembly; and
    third and fourth conductors mechanically and electrically coupled to the third and fourth electrodes.

10. The system of claim 9, wherein the lead body includes a second conductor lumen and a third conductor lumen, wherein the third and fourth conductors are cable conductors disposed, respectively, within the second and third conductor lumens.

11. The system of claim 9, wherein the first, second, third, and fourth conductors are arranged as individual filars in a single, quad-filar coil, and wherein each of the individual filars is electrically insulated from each of the other filars.

12. The system of claim 1, wherein the pulse generator is configured to selectively transmit an electrical stimulus to the first electrode or the second electrode.

13. A system comprising:
    a pulse generator configured to generate an electrical pacing stimulus;
    a separable, splittable or slittable guide catheter configured to deliver electrical stimulation to a His bundle of a patient's heart, the catheter comprising:
        a proximal shaft having a proximal end;
        a pre-curved distal portion extending distally from the proximal shaft and terminating in a distal tip, the distal portion including a series of contiguous preformed curved segments, each having a different radius of curvature and extending along a different arc length than each immediately adjacent segment, the distal portion being configured to locate the distal tip proximate an atrial wall of the heart adjacent the His bundle when the proximal shaft portion is at least partially located in a superior vena cava of the heart;
        an open lumen extending longitudinally from the proximal end of the proximal shaft to the distal tip of the pre-curved distal portion;
        at least one electrode proximate the distal tip; and
        an electrically conductive member extending from at least the proximal end of the proximal shaft to the electrode for electrically coupling the electrode to an external device for mapping electrical activity of the heart;
    an implantable medical electrical lead sized to be slidably received within the open lumen of the catheter, the lead comprising:
        a proximal connector assembly configured to mechanically and electrically couple the lead to the pulse generator;
        a flexible tubular body dimensioned to extend at least partially intravascularly from the pulse generator through the patient's superior vena cava to a location proximate the His bundle, the body including a proximal end coupled to the proximal connector, a distal end opposite the proximal end, and a longitudinal conductor lumen extending from the proximal end of the body to the distal end of the body;

a distal tip assembly fixedly coupled to the distal end of the body, the tip assembly comprising:

a first electrode positioned adjacent to the distal end of the body;

a fixation helix fixedly coupled to the body and extending distally of the first electrode, the fixation helix operable as a second electrode electrically isolated from the first electrode, the fixation helix further dimensioned to extend from a wall of a right atrial septum to a location proximate the His bundle; and a shank portion extending proximally of the first electrode and the fixation helix within the conductor lumen, the shank portion including a proximal face having a receptacle for receiving and engaging a stylet tip, wherein the distal tip assembly includes a tapered distal tip, wherein the fixation helix extends distally of the tapered distal tip, and wherein the first electrode is located on the tapered distal tip;

a first coil conductor extending longitudinally through the conductor lumen and electrically and mechanically coupled to the first electrode; and a second coil conductor extending longitudinally through the conductor lumen and electrically and mechanically coupled to the fixation helix, wherein one or both of the first and second conductors defines a stylet lumen; and a stylet having a proximal end and a distal end including an engaging feature configured to mate with and engage the receptacle on the shank portion of the distal tip assembly, the stylet being configured to transmit a torque applied at its proximal end to the distal tip assembly to cause rotation of the fixation helix and the body.

14. The system of claim 13, wherein an insulating material is disposed between the first electrode and the fixation helix to electrically isolate the first electrode and the fixation helix.

15. The system of claim 13, wherein the first and second electrodes are co-radially disposed.

16. The system of claim 13, wherein a torque transfer ratio of the body and the fixation helix is about 1:1.

* * * * *